United States Patent
Loewe et al.

(10) Patent No.: US 7,696,249 B2
(45) Date of Patent: Apr. 13, 2010

(54) DIPHENYL UREA DERIVATIVES

(75) Inventors: Ralf Loewe, Arlesheim (CH); Sergio Lociuro, Reinach (CH); Stephen Hawser, St. Louis (FR); Laurent Schmitt, Village Neuf (FR)

(73) Assignee: ARPIDA AG, Reinach (CH)

( * ) Notice: Subject to any disclaimer, the term of this patent is extended or adjusted under 35 U.S.C. 154(b) by 0 days.

(21) Appl. No.: 12/096,831

(22) PCT Filed: Dec. 8, 2006

(86) PCT No.: PCT/EP2006/011795

§ 371 (c)(1),
(2), (4) Date: Aug. 27, 2008

(87) PCT Pub. No.: WO2007/068395

PCT Pub. Date: Jun. 21, 2007

(65) Prior Publication Data

US 2009/0005452 A1    Jan. 1, 2009

Related U.S. Application Data

(63) Continuation of application No. PCT/EP2005/013345, filed on Dec. 13, 2005.

(51) Int. Cl.
*A61K 31/17* (2006.01)
*C07C 335/16* (2006.01)
*C07C 275/28* (2006.01)

(52) U.S. Cl. .................. 514/585; 514/596; 564/29; 564/54

(58) Field of Classification Search .................. 514/585, 514/596; 564/29, 54
See application file for complete search history.

(56) References Cited

U.S. PATENT DOCUMENTS

| 2,745,874 A | 5/1956 | Shetty et al. |
| 3,689,550 A | 9/1972 | Schellenbaum et al. |
| 5,057,539 A | 10/1991 | Neukom et al. |
| 7,528,255 B2 * | 5/2009 | Riedl et al. .................. 546/290 |

FOREIGN PATENT DOCUMENTS

| CH | 431 491 | 3/1967 |
| GB | 1 326 481 | 8/1973 |
| WO | WO-01/51456 A2 | 7/2001 |

OTHER PUBLICATIONS

Wikler, M.D., et at, "Methods for Dilution Antimicrobial Susceptibility Tests for Bacteria That Grow Aerobically; Approved Standard - Seventh Edition", vol. 26, No. 2, M7-A7, pp. 1-49 (2006).
Hecht, M.D., et at "Methods for Antimicrobial Susceptibility Testing of Anaerobic Bacteria; Approved Standard - Sixth Edition", vol. 24. No. 2, M11-A6, pp. 1-45 (2004).

* cited by examiner

*Primary Examiner*—Peter G O'Sullivan
(74) *Attorney, Agent, or Firm*—Dickstein, Shapiro, LLP.

(57) ABSTRACT

The invention relates to novel specifically trifluoromethyl and halogen substituted 1,3-diphenyl ureas and their use as active ingredients in the preparation of pharmaceutical compositions. The invention also concerns related aspects like the preparation of the compounds, pharmaceutical compositions containing one or more of those compounds and especially their use as anti-infectives.

14 Claims, No Drawings

DIPHENYL UREA DERIVATIVES

The present invention relates to novel 1,3-diphenyl ureas which are specifically trifluoromethyl and halogen substituted in the phenyl rings, to pharmaceutical compositions containing them and to their use in the treatment and/or prevention of bacterial infections.

In the prior art certain 1,3-diphenyl ureas have been claimed for their insecticidal properties (U.S. Pat. No. 2,745,874) or for a general biocidal activity for combating insects, fungi and infesting herbs (GB Patent Specification 1 326 481). In one instance, the possibility that the insecticidal properties of 1,3-diphenyl ureas might be flanked by a bactericidal action, e.g., against S. aureus and fungicidal activity has been described (U.S. Pat. No. 2,745,874). In addition, certain 1,3-diphenyl ureas have been described as inhibitors of bacterial RNA-polymerase and this property was claimed to often translate into antibacterial activity against aerobic Gram-positive and Gram-negative pathogens, e.g., against S. aureus and E. coli (ToIC) (WO 01/51456).

It has now been found that a small group of novel 1,3-diphenyl ureas with a distinct halogen/trifluromethyl substitution pattern are specifically active against bacteria and exhibit virtually no activity against fungi and that these novel 1,3-diphenyl ureas are very potent against a broad range of aerobic and anaerobic Gram-positive pathogens including, among others, multi-drug resistant staphylococci, e.g., S. aureus and S. epidermidis, enterococci, e.g., E. faecalis, streptococci, e.g., S. pneumoniae, S. pyogenes and S. viridans. These properties render these compounds very useful in the treatment of Gram-positive bacterial infections in humans and animals and/or in the decolonization of sites infested by these pathogens and/or in preventing colonization of sites from which bacteria can then spread and potentially cause bacterial infections. Preferred applications for the compounds of the present invention are those related to the topical/localized treatment of infections in humans and in animals and to the decolonization and/or prevention of colonization of any site which is needed to be rendered sterile from bacteria or in which the bacterial load has to be decreased to prevent spread of bacteria to other sites and to cause infections. Examples of these applications are treatment of skin, mucosal, ocular, dental, gastro-intestinal and upper respiratory-tract infection, decolonization and/or prevention of bacterial colonization of, among others, skin, eyes, nares, mouth, mucosa, gastro-intestinal tract, upper respiratory tract, prosthetic devices and surfaces in general where bacteria can survive and eventually replicate e.g., before surgical practice and/or in general in any instance in which decolonization and/or prevention of spread of bacteria to other sites, which bacteria can infect or colonize, is required.

Therefore, the present invention relates to novel compounds of the general formula I

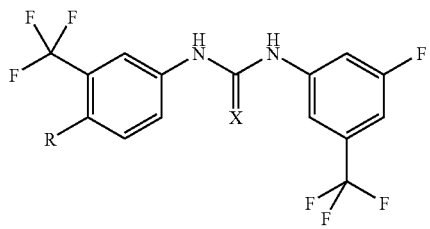

Formula I wherein
R represents chlorine or bromine;
X represents oxygen or sulfur;
and pharmaceutically acceptable salts thereof.

Preferred are compounds of formula I wherein R represents chloro.

Also preferred are compounds where X represents oxygen.

Most preferred compound of the present invention is:
1-(3-Fluoro-5-trifluoromethyl-phenyl)-3-(4-chloro-3-trifluoromethyl-phenyl)-urea, and pharmaceutically acceptable salts thereof.

The expression pharmaceutically acceptable salts encompasses salts with a strong base like an alkali or earth alkali base, e.g. sodium hydroxide, potassium hydroxide, calcium hydroxide etc., or e.g. choline etc.

Because of their ability to inhibit aerobic and anaerobic Gram-positive bacteria, compounds of this invention can be used for the treatment of human and animal diseases which are typically associated with one or more of such type of pathogens and/or in the decolonization of and/or in the prevention of colonization by one or more of such type of bacteria. This makes compounds of this invention valuable antibacterial agents.

The described compounds can be administered by all means known in the art such as, among others, orally, intravenously, topically, rectally, vaginally, sublingually, by inhalation or by any means of local delivery depending on the site were bacteria are localized as colonizers or as infecting agents.

Examples of applications are capsules, tablets, orally administered suspensions or solutions, suppositories, injections, eye-drops, ointments, aerosols/nebulizers or topical/localy administered forms. Examples of topical forms and of forms suitable for local delivery can be, among others, gels, creams, ointments, pastes, lotions, solutions, sprays, lozenges, tablets, capsules, sachet, suspension, suppositories, ovules, lacquers, cements, etc. depending on the site that is intended to treat and/or is intended to reach and/or is intented to protect from colonisation, e.g., skin, mucosa, eye, ear, mouth, nares, parts of the gastro-intestinal tract or of the upper-respiratory tract, prosthetic devices.

The described compounds can be also incorporated in the cement and/or in parts of a prosthetic device from which they are released in order to prevent its colonization.

Preferred applications are oraly, topicaly as well as eye drops.

The dosage used depends upon the type of the specific active ingredient, the use in animal or human, the kind of administration and in case of application in man, the age and the requirements of the patient. Generally, dosages of 0.01-50 mg/kg body weight per day either as a single or subdivided in 2 to 4 doses per day are considered. For liquid or semi-solid formulations, e.g. solutions, ointments, gels or creams an apropiate amount of a formulation with a ratio between the active ingredient and the excipients in a range between 0.01% to 5% are considered. These dosage should be administered preferably in 1 to 4 doses per day which are of equal amounts. As usual children should receive lower doses which are adapted to body weight and age.

The preparations with compounds of formula I can contain inert excipients or also excipients with antibacterial activity. Tablets or granules, for example, could contain a number of binding agents, filling excipients, carrier substances or diluents.

The compositions outlined above may be administered in enteral, oral form or in topical form e.g. as tablets, dragees, gelatine capsules, emulsions, solutions, creams, ointment or suspensions, in intranasal form like sprays or rectally in form of suppositories. These compounds may also be administered parenteral, in intramuscular or intraveneous form, e.g. in form of injectable solutions.

These pharmaceutical compositions may contain the compounds of formula I as well as their pharmaceutically acceptable salts in combination with inorganic and/or organic excipients which are usual in the pharmaceutical industry like lactose, maize or derivatives thereof, talcum, stearinic acid or salts of these materials.

For gelatine capsules vegetable oils, waxes, fats, liquid or half-liquid polyols etc. may be used. For the preparation of solutions and syrups e.g. water, polyols, saccharose, glucose etc. are used. Injectables are prepared by using e.g. water, polyols, alcohols, glycerin, vegetable oils, lecithin, liposomes etc. Suppositories are prepared by using natural or hydrogenated oils, waxes, fatty acids (fats), liquid or half-liquid polyols etc. For the preparation of creams, gels, ointments etc. for topical and/or local applications e.g. polyols, oils, detergents, penetration enhancer, fillers etc. are used which are known to someone skilled in the art.

The compositions may contain in addition preservatives, stabilisation improving substances, viscosity improving or regulating substances, solubility improving substances, sweeteners, dyes, taste improving compounds, salts to change the osmotic pressure, buffer, antioxidants etc.

The compounds of formula I may also be used in co-therapy with one or more other therapeutics, for example with other classes of anti-infective agents to increase/complement their anti-infective spectrum of action, e.g. penicillins and cephalosporins; glycopeptides; quinolones; tetracyclines; aminoglycosides; macrolides, sulfonamides etc. or antifungals, antiprotozals etc.

Compounds of this invention can be also incorporated in cleaning and/or cleansing solutions and/or dressings and/or coatings and/or lacquers and/or cements and/or parts of a prosthetic device for decolonization and/or prevention of bacterial colonization of sites in which bacteria can survive and eventually replicate causing potential risk for infections.

Compounds of formula I can be generally synthesized by reacting—as depicted in Scheme 1 below—a 4-halo-5-(trifluoromethyl)-phenyl-isocyanate or corresponding phenyl-thioisocyanate of formula IIa with a 3-fluoro-5-trifluoromethyl-aniline IIIa (see also experimental part). Alternatively a 4-halo-5-(trifluoromethyl)-aniline of formula IIb can be coupled with a 3-fluoro-5-(trifluoromethyl)-phenyl-isocyanate or 3-fluoro-5-(trifluoromethyl)-phenyl-thioisocyanate IIIb to yield derivatives of the general formula I.

Scheme 1

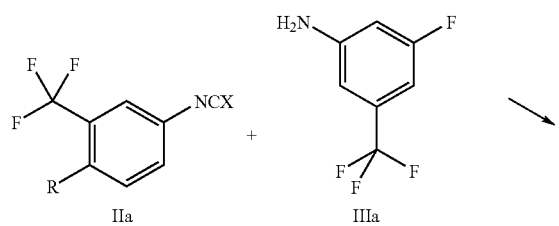

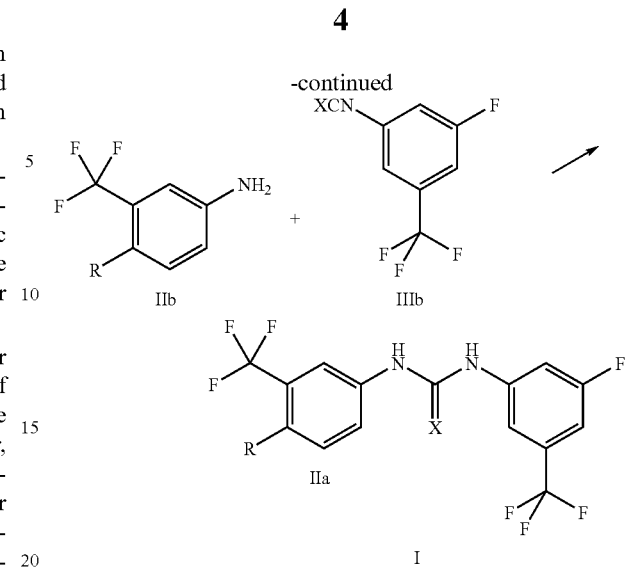

EXAMPLES

Abbreviations:
DMF: N,N-Dimethyl formamide
DMSO: Dimethyl sulfoxide
EtOAc: Ethyl acetate
MS: Mass spectrometry
NMR: Nuclear magnetic resonance
TBME: tert-Butyl methyl ether
THF: Tetrahydrofuran
cHexane: Cyclohexane
sat.: saturated
rt: room temperature
r.m.: reaction mixture Example 1

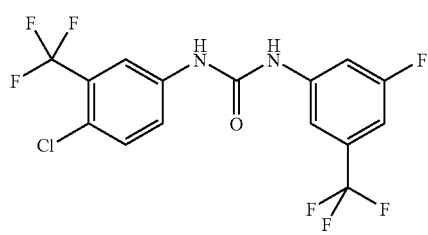

1-(3-Fluoro-5-trifluoromethyl-phenyl)-3-(4-chloro-3-trifluoromethyl-phenyl)-urea To a solution of 3-Fluoro-5-trifluoromethyl-aniline (940 mg, 5.25 mmol, 1.05 eq.) in dry THF (20 ml) was added 4-Chloro-3-(trifluoromethyl)-phenylisocyanate (1.11 g, 5.0 mmol) at rt and the mixture was stirred overnight. Then it was diluted with cHexane (100 ml), washed twice with 2 N HCl, once with sat. NaHCO$_3$ and brine (100 ml each) and adsorbed on Celite in vacuo. Flash chromatography on silica with cHexane/TBME (5:1 to 3:1) yielded 687 mg pure product (34%) as a white powder.

$^1$H NMR (DMSO) δ 9.41 (s, 2H), 8.09 (d, J=2.4 Hz, 1H), 7.6-7.7 (m, 4H), 7.25 (d, J=8.1, 1H). MS (ES$^-$): 398.9.

Example 2

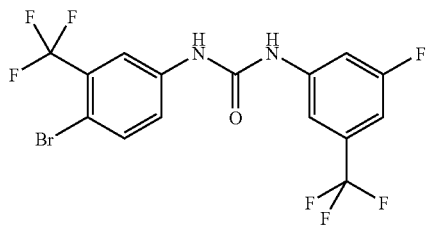

1-(3-Fluoro-5-trifluoromethyl-phenyl)-3-(4-bromo-3-trifluoromethyl-phenyl)-urea

To a solution of 4-Bromo-3-(trifluoromethyl)-aniline (132 mg, 0.55 mmol, 1.1 eq.) in dry THF (5 ml) was added 3-Fluoro-5-(trifluoromethyl)-phenylisocyanate (72 μl, 0.5 mmol). After stirring overnight at rt the mixture was diluted with cHexane (20 ml), washed twice with 2 N HCl, once with sat. NaHCO$_3$ and brine (20 ml each) and adsorbed on Celite in vacuo. Flash chromatography on silica with cHexane/TBME (4:1 to 2:1) yielded 111 mg product (50%) as a white powder.

MS (ES$^-$): 442.9, 444.9.

Example 3

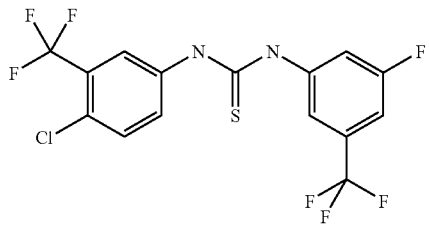

1-(3-Fluoro-5-trifluoromethyl-phenyl)-3-(4-chloro-3-trifluoromethyl-phenyl)-thiourea The title compound was synthesized according to the procedure used in example 2 starting with 3-Fluoro-5-(trifluoromethyl)-aniline and 4-Chloro-3-(trifluoromethyl)-phenyl-isothiocyanate. Yield: 98 mg (47%).

MS (ES$^-$): 414.9.

Example 4

Biological Results

Antimicrobial susceptibility testing was performed in accordance with the Clinical and Laboratory Standards Institute (CLSI).

Clinical and Laboratory Standards Institute (CLSI; formerly NCCLS): Methods for Dilution Antimicrobial Susceptibility Tests for Bacteria That Grow Aerobically; Approved Standard—Seventh Edition (2006). Clinical and Laboratory Standards Institute document M7-A7.

Streptococci (*S. pneumoniae*, *S. pyogenes*, *S. viridans*) were tested following the CLSI methodology with the exception that Todd Hewitt Broth without blood was used. Anaerobic bacteria (*P. acnes*, *B. distasonis*) were tested following CLSI (formerly NCCLS) guidelines except for using microbroth dilutions in Wilkins Chalgren Broth. National Committee for Clinical Laboratory Standards (NCCLS). Methods for Anti-microbial Susceptibility Testing of Anaerobic Bacteria; Approved Standard—Sixth Edition (2004). NCCLS document M11-A6.

A) In vitro Antibacterial Activity of Compounds Against Representative Pathogens for Nasal Colonization

| | (Minimum Inhibitory Concentration (MIC) in micrograms/ml) | | | |
|---|---|---|---|---|
| Example | S. aureus ATCC 25923 | S. aureus MRSA 101 | S. aureus MRSA 39 | S. epidermidis MRSE 70 |
| 1 | 0.125 | 0.125 | 0.125 | 0.25 |
| 2 | 0.125 | 0.25 | 0.125 | 0.5 |
| 3 | 0.25 | 0.25 | 0.25 | 0.25 |

B) In vitro Antibacterial Activity of Compounds Against Representative Pathogens for Ocular Infections

| | (Minimum Inhibitory Concentration (MIC) in micrograms/ml) | | | | | |
|---|---|---|---|---|---|---|
| Example | S. aureus 25923 | S. aureus MRSA 101 | S. aureus MRSA 39 | S. epidermidis MRSE 70 | S. pneumoniae 1/1 | S. pyogenes GAS-1 |
| 1 | 0.125 | 0.125 | 0.125 | 0.25 | 0.06 | 0.125 |
| 2 | 0.125 | 0.25 | 0.125 | 0.5 | ≦0.03 | 0.06 |
| 3 | 0.25 | 0.25 | 0.25 | 0.25 | 0.5 | 0.5 |

C) In vitro Antibacterial Activity of Compounds Against Representative Pathogens for Skin Infections

| (Minimum Inhibitory Concentration (MIC) in micrograms/ml) | | | | | |
|---|---|---|---|---|---|
| Example | S. aureus MRSA 39 | S. epidermidis MRSE 70 | S. pyogenes GAS-1 | E. faecalis VanB E80-8 | P. acnes 6390 |
| 1 | 0.125 | 0.25 | 0.125 | 1 | ≦0.03 |
| 2 | 0.125 | 0.5 | 0.06 | 1 | ≦0.03 |
| 3 | 0.25 | 0.25 | 0.5 | 2 | ≦0.03 |

D) In vitro Antibacterial Activity of Compounds Against Representative Pathogens for Gastro-Intestinal* or Dental** Infections

| (Minimum Inhibitory Concentration (MIC) in micrograms/ml) | | | |
|---|---|---|---|
| Example | E. faecalis* VanB E80-8 | B. distasonis* 5770 | S. viridans** UHC 7 |
| 1 | 1 | 0.25 | 0.5 |
| 2 | 1 | 0.25 | 0.5 |
| 3 | 2 | 0.5 | 2 |

The invention claimed is:

1. A compound of formula I

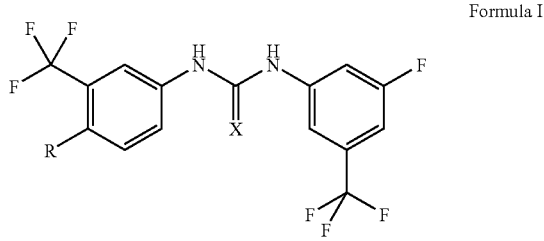

Formula I wherein
R represents chlorine or bromine;
X represents oxygen or sulfur; and
pharmaceutically acceptable salts thereof.

2. The compound according to claim 1, wherein R represents chloro.

3. The compound according to claim 1 or 2, wherein X represents oxygen.

4. 1-(3-Fluoro-5-trifluoromethyl-phenyl)-3-(4-chloro-3-trifluoromethyl-phenyl)-urea, and pharmaceutically acceptable salts thereof.

5. A pharmaceutical composition for the treatment of infections, comprising the compound of claim 1 and usual carrier materials and adjuvants.

6. A pharmaceutical composition for the treatment of infections caused by aerobic and anaerobic Gram positive and anaerobic Gram negative pathogens, comprising the compound of claim 1 and usual carrier materials and adjuvants.

7. The compound of claim 1 for use as medicaments for the treatment of infections.

8. The compound of claim 1 for use as medicaments for the treatment of infections caused by aerobic and anaerobic Gram positive and anaerobic Gram negative pathogens.

9. The compound of claim 1 for use as active ingredients for the production of pharmaceutical compositions for the treatment of infections.

10. A method for the treatment of infections caused by aerobic and anaerobic Gram positive and anaerobic Gram negative pathogens, comprising administering to a patient a therapeutically effective amount of a pharmaceutical composition containing a compound of claim 1 as an active ingredient.

11. A method for the treatment of bacteria causing nasal, ocular, dental, gastro-intestinal or skin infections, comprising administering to a patient a therapeutically effective amount of a pharmaceutical composition containing a compound of claim 1 as an active ingredient.

12. A method for the sterilisation, sanitation, antisepsis, disinfection, decolonisation or prevention of colonisation of the skin, gastro-intestinal tract or the nasal, ocular or dental area or any type of prosthetic device, comprising administering a therapeutically effective amount of a pharmaceutical composition containing a compound of claim 1 as an active ingredient.

13. A process for the manufacture of the pharmaceutical composition of claim 1 as an active ingredient for the treatment of infections, comprising mixing at least one active ingredient with a pharmaceutically acceptable excipient.

14. A process for the manufacture of the pharmaceutical composition of claim 1 as an active ingredient for the treatment of infections caused by aerobic and anaerobic Gram positive and anaerobic Gram negative pathogens, comprising mixing at least one active ingredient with a pharmaceutically acceptable excipient.

* * * * *